US008414947B2

(12) United States Patent
Adelmann et al.

(10) Patent No.: US 8,414,947 B2
(45) Date of Patent: Apr. 9, 2013

(54) PHARMACEUTICAL PREPARATION THAT CAN BE ADMINISTERED ORALLY FOR TREATING FISH, PRODUCTION METHOD FOR SAID PREPARATION AND USE OF THE LATTER

(75) Inventors: Malte Adelmann, Greifswald (DE); Dieter Fichtner, Greifswald (DE); Bodo Lange, Greifswald (DE); Werner Weitschies, Neuenkirchen (DE)

(73) Assignee: Riemser Arzneimittel AG, Greifwald-Insel Riems (DE)

( * ) Notice: Subject to any disclaimer, the term of this patent is extended or adjusted under 35 U.S.C. 154(b) by 0 days.

(21) Appl. No.: 11/817,266

(22) PCT Filed: Dec. 13, 2005

(86) PCT No.: PCT/EP2005/013497
§ 371 (c)(1),
(2), (4) Date: Dec. 6, 2007

(87) PCT Pub. No.: WO2006/092168
PCT Pub. Date: Sep. 8, 2006

(65) Prior Publication Data
US 2008/0317825 A1 Dec. 25, 2008

(30) Foreign Application Priority Data
Mar. 2, 2005 (DE) .................. 10 2005 010 288

(51) Int. Cl.
*A23D 9/013* (2006.01)
*A61K 39/385* (2006.01)
(52) U.S. Cl. ...... 426/531; 426/805; 424/827; 424/184.1
(58) Field of Classification Search .................. None
See application file for complete search history.

(56) References Cited

U.S. PATENT DOCUMENTS 6,274,147 B1 * 8/2001 Vakharia et al. ........... 424/199.1
6,566,117 B2 * 5/2003 Chi .............................. 435/235.1

FOREIGN PATENT DOCUMENTS

| WO | 89 05154 A | 6/1989 |
| WO | 01 54514 A | 8/2001 |
| WO | 03 086097 A | 10/2003 |
| WO | WO 03/086097 | * 10/2003 |

OTHER PUBLICATIONS

Aksnes et al. Aquaculture (1997) 153, p. 251-261.*
Shao, Advanced Drug Delivery Reviews (2001) vol. 50, p. 229-243.*
Estepa et al. Journal of General Virology (1994) 75, p. 1329-1338.*
Shao et al. Aquaculture pharmaceuticals and biologicals: current perspectives and future possibilities. Advanced Drug Delivery Reviews, 2001, vol. 50, 229-243.*
Lecocq-Xhonneux et al. A recombinant viral haemorrhagic septicaemia virus glycoprotein expressed in insect cells induces protective immunity in rainbow trout. Journal of General Virology, 1994, vol. 75, 1579-1587.*
Gill, Starter aquafeeds: Breaking the 1.5mm barrier, 2004, www.Aquafeed.com, <<accessed online at http://www.aquafeed.com/read-article.php?id=34&sectionid=4>> on Feb. 2, 2011.*
Sommerset et al., Vaccines for fish in aquaculture, 2005, Expert Reviews in Vaccines, vol. 4, No. 1, pp. 89-101.*

* cited by examiner

Primary Examiner — Benjamin P Blumel
(74) Attorney, Agent, or Firm — Norris McLaughlin & Marucs, P.A.

(57) ABSTRACT

The present invention is directed to a pharmaceutical preparation for oral application for treatment of fish, in particular for vaccination of fish of the salmon family and other fish having a comparable digestive system against bacterial and/or viral infections, in particular against VHS and IHN. The invention is also directed to a method for producing the preparation.

4 Claims, 1 Drawing Sheet

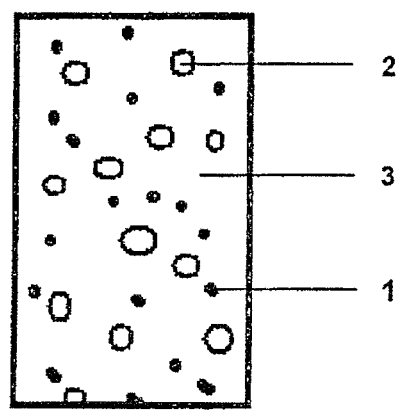

PHARMACEUTICAL PREPARATION THAT CAN BE ADMINISTERED ORALLY FOR TREATING FISH, PRODUCTION METHOD FOR SAID PREPARATION AND USE OF THE LATTER

The present invention is directed to a pharmaceutical preparation for oral application for treatment of fish, in particular for vaccination of fish of the salmon family and other fish having a comparable digestive system against bacterial and/or viral infections, in particular against VHS and IHN. The invention is also directed to a method for producing the preparation.

Epidemics in fish, such as viral hemorrhagic septicemia (VHS) and infectious haematopoietic necrosis (INH) of the salmon family, in particular trout, still pose a significant problem for the fish industry in spite of extensive eradication measures, such as keeping the fish in fish farms that have been verified to be disease-free. During the past several years in Germany alone, between 34 and 80 new cases of these viral diseases have been reported each year. Once a population is infected, the mortality rate of the fish can reach 90%. New cases of VHS and IHN result in large economic losses, with yearly losses in the European Union estimated to be between 12 and 36 million Euro. Prophylactic immunization offers one possibility for a concerted effort to fight diseases in fish. Vaccination of fish has not yet been instituted worldwide, but is essential for many fish farms and farming methods. However, the use of the vaccines has been limited by their high production costs, their lack of user friendliness and a relatively low efficacy.

A widely used method for immunizing fish is intraperitoneal injection. The fish are hereby anesthetized by immersion into an anesthetic solution and the corresponding dose is injected into the abdominal cavity of each specimen. This type of immunization produces very high protection rates and is viewed as the most effective method. However, this method is time-consuming and hence unsuitable for immunizing large populations and can therefore be applied in an extensive aquaculture only on a limited basis. In addition, this application method subjects the fish to considerable stress, and losses can be expected as a result of the anesthesia. The application method is also very expensive and immunization by automatic injection machines is complex. In spite of the very encouraging results, this type of vaccination has not been widely accepted.

Another method for vaccinating fish is immersion. One example is immunization in a bath. The specimen to be vaccinated are hereby immunized by placing the fish in an immersion bath for a specified time period. This method was tested with inactivated bacteria and attenuated viruses. However, the fish are here also exposed to enormous stress. Since the protection rates are acceptable only with certain limitations, this method has so far not found wide acceptance in practice. Another type of immersion is a spray method. The species to be immunized on here sprayed with an antigen solution in a meander pattern. The vaccine is absorbed by the mucus membrane and shows varying success, depending on the type of the antigen. This method, too, has only limited practical use.

Studies for immunization of fish by DNA vaccination has been reported in the literature. A DNA plasmid, which codes for particular proteins with antigen character of, for example, virus (VHS), is here intramuscularly injected in the fish. The results confirm a high protection rate; however, this method is presently only used on an experimental scale.

Oral vaccination is presently the simplest method for immunizing a large number of fish [Irie, T., Watarai, S., Kodama, H.: Humoral immune response of carp (*Cyprinus carpio*) induced by oral immunization with liposome-entrapped antigen. *Developmental & Comparative Immunology* 27 (2002), 413-421]. The liquid or lyophilized vaccines are either added to the feed stock or are processed into a solid drug form which can be applied orally. Oral immunization can advantageously be applied to large numbers of fish and to fish of any age. Moreover, the application is stress-free and user-friendly. Drug forms which can be applied orally and which have been tested to date show a comparatively low efficacy and require a complicated and expensive production process.

For oral application, the vaccine must pass through the gastric tract (pH 2-4) which in many fish species is acidic. The effect from the gastric acid can inactivate the vaccine, thus limited the amount of protection. Drug forms for oral immunization of fish developed to date are designed in such a way that the pellets pass through the stomach without disintegrating and release the active ingredient in the intestine of the fish. Therefore, it is known to protect the vaccine from inactivation by the gastric acid by a gastric-acid-resistant coating. However, the coating process can cause a substantial decrease in the normality due to the frequently very high temperatures and the fact that many coating materials that resist gastric acid are themselves organic acids which can inactivate the vaccine at the surface. Moreover, it cannot be ensured that these drug forms fully protect the vaccines, because measurements have shown that these preparations remain in the stomach of up to 24 hours. A complete release of the vaccines in the intestines is also questionable, because release of the vaccines may be delayed when the drugs are coated. Moreover, producing the gastric-acid-resistant coatings is very expensive.

Attempts have also been made to incorporate the vaccine into a lipid (hard fat) and to orally administer the preparations produced by a dripping method. It is postulated that the vaccines are released in the intestine of the fish by enzymatical digestive processes. However, more detailed investigations have shown that this lipid is digested by the fish either not at all or only incompletely, thereby preventing release of the vaccine from this type of drug.

DE 197 41 114 A1 describes a preparation for oral immunization of rainbow trout. The vaccine is incorporated into a mixture of lactose and starch, and optionally a binder (gelatin or other commonly used substances) and then granulated with a gastric-acid-resistant matrix former (for example, a macromolecular cellulose compound or an ion exchanger) by way of fluidized bed granulation or screen press extrusion. The matrix former is intended to prevent premature release in an acidic environment. The granulate is pressed into tablets and is covered in a fluidized bed process with gastric-acid-resistant copolymers of acrylic acid so as to become stable against water and acids.

DE 16 17 300 OS describes an oral, doubly encapsulated gastric-acid-resistant drug form for immunizing humans, which protects the attenuated adeno virus from inactivation during the production process. The antigen-containing core of the tablet is here provided with an inert, pressed-on coating made of lactose, magnesium stearate, and microcrystalline cellulose which reliably protects the viruses during coating with a gastric-acid-resistant copolymer (cellulose acetate hydrogen phthalate).

DD 259 13 A1 describes a drug form available for oral administration of live and inactivated vaccines to fish. The preparation includes an active vaccine agent, in particular a vaccine against VHS, and lactose as a filler, embedded in a fat or a lipoid substance. The preparation is produced by suspending the active vaccine agent in the lipophillic carrier material, which is heated to between 22 and 27° C., followed by instilling the suspension into an indifferent liquid (e.g., an ethanol-water mixture). The lipophillic carrier material prevents release of the active ingredient in the stomach and the upper intestinal tract.

All the aforementioned publications describe drug forms where the vaccine is protected from the inactivating effect of the gastric acid by embedding the vaccine and/or by gastric-acid-resistant coatings. In general, the preparation then passes through the stomach without disintegrating and only disintegrates in the intestine. The potential disadvantages have already been described above.

It is an object of the present invention to provide a preparation for the treatment of fish, in particular for vaccination of fish, which can be produced cost-effectively and administered orally, and which ensures passage of the vaccine through the gastric tract of fish without loss. The antigen is intended to be completely released in the fish to offer adequate protection during a stress-induced infection.

The object is attained by a pharmaceutical preparation for the treatment of fish, in particular for vaccination of fish of the salmon family, against bacterial and/or viral infections, which can be administered orally and which includes at least one pharmacologically active ingredient, at least one basic additive component, and at least one carrier component, wherein the preparation is formulated so as to disintegrate at least partially, in particular to at least 80%, preferably almost completely, in an acidic environment in the stomach of the fish to be immunized. The formulation according to the invention is characterized by a novel release system which, unlike conventional concepts, does not intend to prevent disintegration of the drug form in the stomach, but instead causes the drug form to disintegrate almost completely already in the stomach of the fish, wherein in addition to the active ingredient, the at least one basic additive component is also released in the stomach for effectively neutralizing and adsorbing the gastric acid (HCl). The so produced local and temporary neutralization protects the pharmacological active ingredient during its passage through the stomach from the inactivating effect of the gastric acid. Studies on fish treated in this way have shown that as a result of the early disintegration, the preparation passes through the gastric tract of the animal much faster. Whereas conventional, gastric-acid-resistant preparations reside in the stomach for up to 24 hours, the preparation according to the invention was already no longer detected in the stomach after approximately 4 hours following oral ingestion, i.e., the disintegrated drug form reaches the intestinal tract completely in 4 hours or less. Both effects—neutralization and shortened passage—ensure that the pharmacologically active ingredient passes through the gastric tract without loss.

Preferably, a fraction of the at least one basic additive component in the preparation is designed so that when the preparation disintegrates in the stomach of the fish to be immunized, a pH value in the range of 6.0 to 8.5 is attained, in particular of 7.0 to 7.5, at least in the surrounding region of the disintegrated preparation. Most acid-labile active ingredients, in particular antigen-containing vaccines, are stable under these largely neutral conditions.

Basic additive components include, in particular, Lewis bases which are substances that dissociate in an aqueous environment by releasing OH ions. Preferably, pharmacologically acceptable inorganic hydroxides are employed, in particular metal hydroxides or mixtures of thereof. It would also be feasible to use other proton-binding bases.

According to a particular advantage of the preparation of the invention, the additive components (in particular the matrix-forming carrier component) necessary for embedding the active ingredient need not be heated for processing. The formulation of the invention therefore makes it feasible to produce the pellets to be administered by cold extrusion. This refers to extrusion without supplying heat or even with applied cooling, i.e., processing at room temperature or at lower temperatures. In this way, the heat-sensitive active ingredient (in particular the vaccine) is not exposed to elevated temperatures during the entire production process, thereby preventing partial inactivation. In contrast, the coating methods of conventional preparations with an acid-resistant layer always involve a heating step and therefore reduce the normality which is undesirable. The preferred production method by cold extrusion reduces requirements for material, time and personnel.

According to the preferred processing method, an extrudable carrier component is preferably used, which has at the processing temperature (in particular room temperature) a highly viscous, in particular semi-fluid to wax-like consistency. According to a preferred embodiment, the carrier component is a high-molecular, natural or synthetic polymer, in particular a polyether (such as polyethylene glycol) or gelatin. Mixtures of these components can also be used.

The preparation of the invention develops its advantageous effect predominantly with pharmacologically active ingredients susceptive to heat and acids. According to a particularly preferred embodiment, this includes at least one active vaccine ingredient with at least one live vaccine or inactivated vaccine, in particular inactivated bacteria and/or attenuated viruses. According to the preferred use of the preparation for immunizing fish, in particular fish of the salmon family, against viral hemorrhagic septicemia (VHS) and/or infectious haematopoietic necrosis (INH), the preparation includes an attenuated aetiological agent of these infections which both belong to the family of Rhabdo viruses.

It will be understood that the preparation may include additional additive components and/or an (acid-labile) coating. More particularly, the preparation and/or the coating may include a dye for improving acceptance of the preparation by fish. Examples are iron oxides having different colors which are used, for example, in the food industry. The color of the extruded materials can be varied for adjustment to different types of fish. The extruded materials can also be mixed with ground fish food to ensure better acceptance. Some degree of temporary stability in water has been achieved by selecting a suitable type and composition of the additive components.

A particularly preferred formulation of the newly developed drug form is an extruded substance having the components virus lyophilisate (active ingredient/vaccine), polyethylene glycol (matrix-forming carrier component), aluminum hydroxide and magnesium hydroxide (alkaline components), iron oxide E 171 (dye) and talcum (coating).

Additional advantageous embodiments of the invention include additional features recited in the dependent claims.

The invention will now be described with reference to an exemplary embodiment.

Production of the Preparation 19.9 g polyethylene glycol (PEG) 1000 and 13.2 g polyethylene glycol 1500 were melted, then frozen for 2 hours at −20° C. and crushed in 50 ml liquid nitrogen with a mortar and pestle. 8.3 g VHS lyophilsate with a virus titer of $10^5$ KID/10 mg were mixed with 3.3 g of each of the neutralizing and adsorbing bases $Mg(OH)_2$ and $Al(OH)_3$ and about 1 g of a food dye E171 iron oxide and then proportionally worked into the crushed polyethylene glycol. The mixture was extruded with a homemade manual extruder and coated with dyed talcum. The produced food pellets (extruded materials) had a length of about 3 mm and a diameter of about 1.7 mm. The titer of the oral vaccine was $10^{4.5}$ KID/g.

The FIGURE shows an enlarged detail of the schematic structure of the extruded preparation prepared in this manner. The reference symbol 1 refers to the pharmacologically active ingredient, i.e., the lyophilized VHS active vaccine ingredient, while the reference symbol 2 refers to the basic components $Mg(OH)_2/Al(OH)_3$. The VHS active vaccine ingredient 1 and the basic component level 2 are encapsulated by a matrix 3 of the PEG carrier (PEG 1000/1500).

Application Test

The extruded substances were fed three times daily for 72 hours. The corresponding quantity was mixed with 2 grams commercial fish food. An infection with a virulent VHS virus was induced 6 weeks after the immunization. Of the orally immunized fish, only 13.5% died after the stress-induced infection. The mortality rate in the control group of fish, which was treated with a placebo without the virus, was 70%. The mortality rates of the two groups are therefore significantly different, with a margin of error of 5%.

The disclosed invention is particularly suited for the production of preparations for oral application of acid-labile viruses and drugs for fish. Advantageously, the concentration or activity of the active ingredients in this drug form is not adversely affected by the production process. Inactivation of the active ingredients by the acidic environment of the stomach can be reliably prevented, so that the vaccine is completely released in the fish. The extruded substances can be produced in large quantities with less material, time and personnel. The oral preparations are suitable for mass vaccination of large fish stock.

The invention claimed is:

1. A method for producing an extruded pharmaceutical preparation for oral administration for vaccination of fish, comprising:

preparing a mixture of at least one active vaccine ingredient, at least one basic inorganic hydroxide component, and at least one carrier component; and extruding the mixture into feed pellets of the extruded preparation via cold extrusion, wherein the at least one active vaccine ingredient and the at least one basic inorganic hydroxide component are encapsulated by a matrix of the at least one carrier component via the cold extrusion to produce the extruded preparation, wherein the extruded preparation is formulated so as to disintegrate by at least 80% in an acidic environment in a stomach of a fish to be vaccinated.

2. The method according to claim 1 wherein the feed pellets are provided with a coating.

3. The method according to claim 2, wherein the coating contains a talcum and/or a dye.

4. The method according to claim 2, wherein the step of extruding is carried out at room temperature or a temperature below room temperature.

* * * * *